(12) United States Patent
Arms et al.

(10) Patent No.: US 6,871,413 B1
(45) Date of Patent: *Mar. 29, 2005

(54) MINIATURIZED INCLINOMETER FOR ANGLE MEASUREMENT WITH ACCURATE MEASUREMENT INDICATOR

(75) Inventors: Steven W. Arms, Burlington, VT (US); Christopher P. Townsend, Shelburne, VT (US)

(73) Assignee: Microstrain, Inc., Williston, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 731 days.

This patent is subject to a terminal disclaimer.

(21) Appl. No.: 08/990,912

(22) Filed: Dec. 15, 1997

(51) Int. Cl.$^7$ .............................. G01C 9/06; G01B 7/30
(52) U.S. Cl. ...................... 33/366.11; 33/1 N; 33/1 PT
(58) Field of Search ............................ 33/366.11, 1 N, 33/1 PT, 511, 512, 534, 304, 313; 340/686.1, 686.2, 689, 500, 501, 502, 503, 514; 600/595

(56) References Cited

U.S. PATENT DOCUMENTS

| | | | |
|---|---|---|---|
| 3,699,316 A | | 10/1972 | Lopes ........................ 702/153 |
| 4,106,094 A | | 8/1978 | Land ........................... 33/312 |
| 4,265,028 A | | 5/1981 | Van Steenwyk ............ 244/175 |
| 4,559,713 A | * | 12/1985 | Ott et al. ...................... 33/302 |
| 4,700,142 A | * | 10/1987 | Kuckes .................... 340/853.5 |
| 4,747,216 A | * | 5/1988 | Kelly et al. .............. 33/366.22 |
| 4,817,633 A | * | 4/1989 | McStravice et al. ........ 600/595 |
| 4,839,838 A | * | 6/1989 | LaBiche et al. ............ 708/141 |
| 4,912,662 A | * | 3/1990 | Butler et al. ................ 702/154 |
| 4,945,647 A | * | 8/1990 | Beneventano et al. ........ 33/321 |
| 5,103,667 A | * | 4/1992 | Allen et al. ................... 73/1.38 |
| 5,163,228 A | * | 11/1992 | Edwards et al. ............. 33/1 N |
| 5,224,469 A | * | 7/1993 | Mocny ....................... 601/108 |
| 5,237,753 A | * | 8/1993 | Carlson et al. ........... 33/366.14 |
| 5,313,968 A | * | 5/1994 | Logan et al. ................ 600/595 |
| RE34,700 E | * | 8/1994 | Suzuki et al. ................. 84/600 |
| 5,335,190 A | * | 8/1994 | Nagle et al. ................. 702/152 |
| 5,342,404 A | * | 8/1994 | Alt et al. ......................... 607/6 |
| 5,375,610 A | * | 12/1994 | LaCourse et al. ........... 600/595 |
| 5,459,676 A | * | 10/1995 | Livingston ............. 364/528.31 |
| 5,469,862 A | * | 11/1995 | Kovacevic .................. 600/595 |
| 5,645,077 A | * | 7/1997 | Foxlin ........................ 600/587 |
| 5,761,818 A | * | 6/1998 | Hopkins et al. .......... 33/366.14 |
| 5,821,414 A | * | 10/1998 | Noy et al. ................ 73/152.54 |
| 5,887,351 A | * | 3/1999 | Arms et al. ................. 33/1 PT |
| 5,955,667 A | * | 9/1999 | Fyfe ............................. 73/490 |
| 5,956,660 A | * | 9/1999 | Neumann .................... 702/150 |
| 5,991,085 A | * | 11/1999 | Rallison et al. ............. 359/630 |
| 6,148,280 A | * | 11/2000 | Kramer ....................... 703/153 |

* cited by examiner

Primary Examiner—Diego Gutierrez
Assistant Examiner—R. Alexander Smith
(74) Attorney, Agent, or Firm—Thomas N. Neiman; James M. Leas

(57) ABSTRACT

The novel miniaturized inclinometer for angle measurement with accurate measurement indicator is designed to monitor the angular motion of limbs. The device contains at least one inclinometer with signal conditioning electronics, including a microprocessor, placed within a miniature housing. A number of different sensors can be used and positioned in their housings so that their outputs vary as a function of their angle with respect to the gravity sector. The microprocessor controls a multiplexer, which controls the activities of the sensors; performs analog to digital conversions and measures the output curves from the sensor pairs to perform a conversion which results in a three hundred and sixty degree range with respect to gravity. Calibration data is stored in a read only memory and the microprocessor corrects variables to ensure accuracy and measures the difference in angle between the pairs of sensors.

69 Claims, 5 Drawing Sheets

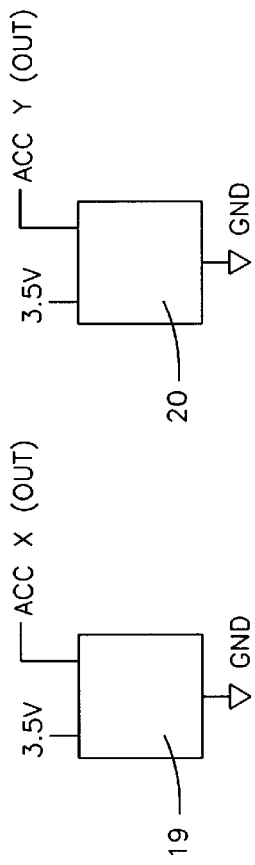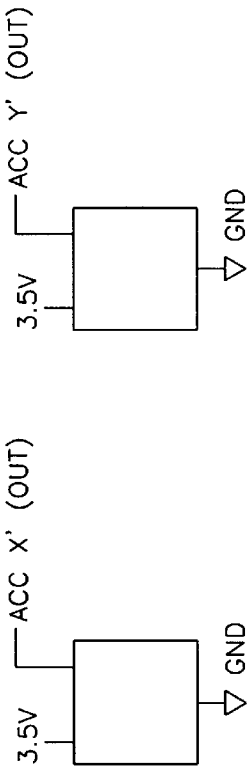
FIGURE 3a
FIGURE 4a
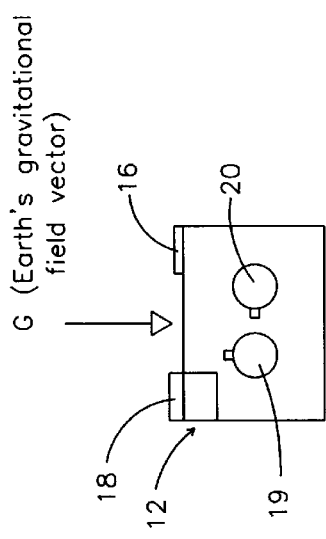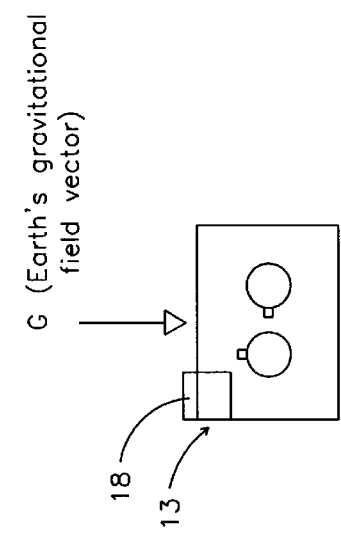
FIGURE 3
FIGURE 4

ANGLE WITH RESPECT TO G →
X Y

ANGLE WITH RESPECT TO G →
X' Y'

US 6,871,413 B1

MINIATURIZED INCLINOMETER FOR ANGLE MEASUREMENT WITH ACCURATE MEASUREMENT INDICATOR

BACKGROUND OF THE INVENTION

This is a utility patent application based upon the provisional application, Ser. No. 60/032,938, filed upon Dec. 9, 1996.

This invention pertains to devices for measuring angles in a small sized instrument and, in particular, to a miniaturized inclinometer for angle measurement with accurate measurement indicator for use in biomedical, industrial, commercial and personal applications, such as measuring the angles of various body joints.

There have been a number of attempts to develop angle measuring units. Examples of this type device are the United States patent issued to Graham, Baillet and Sankey U.S. Pat. No. 4,442,606 issued on Apr. 17, 1984 for a Digital Goniometer is an example of this typical units. Other attempts in this area include the United States patents issued to Joyal et al, U.S. Pat. No. 3,996,670 issued on December 1976 and to Beck, U.S. Pat. No. 4,249,314 issued in February 1981. There are, however many difficulties with those type devices. Among the difficulties are moisture problems, problems created by dirt and limitations of visibility and motion. Potentiometers wear out over time, usually have a travel stop which limits their rotatability and are not transparent.

What is needed is an inclinometer for angle measurement with an accurate measurement indicator that does not wear out over time and has an unlimited 360 degree resolution. What is needed is a unit that senses errors in the measurements and provides notification to the user or such errors. What is needed is an assembly which is simple and easy to use, has a complete range of motion and allows complete visibility for the operator to measure any desired angle. What is also needed is signal sending means that allows the data from the sensors to be processed by a micro controller or personal computer or computer network.

It is the object of this invention to teach a miniaturized inclinometer for angle measurement with accurate measurement indicator which avoids the disadvantages and limitations, recited above in similar systems. Another object of this invention is to provide an system that is extremely efficient and accurate.

SUMMARY OF THE INVENTION

Particularly, it is the object of this invention to teach a miniaturized inclinometer for angle measurement with accurate measurement indicator, for use in medical, industrial, commercial and personal applications to monitor the angular position of limbs among a plurality of other applications, comprising at least one housing; sensor means positioned within said housing; and an electrical control and measurement system for collecting data and calculating said angles over a full three hundred and sixty degree range.

BRIEF DESCRIPTION OF THE DRAWINGS

Further objects and features of this invention will become more apparent by reference to the following description taken in conjunction with the following figures, in which:

FIG. 3 is an internal view of the sensors 19 and 20 thereof;

FIG. 3a is an exploded view of FIG. 3;

FIG. 4 is an internal view of the sensors 36 and 37 thereof;

FIG. 4a is an exploded view of FIG. 4;

DETAILED DESCRIPTION OF THE PREFERRED EMBODIMENT

Figure 1:
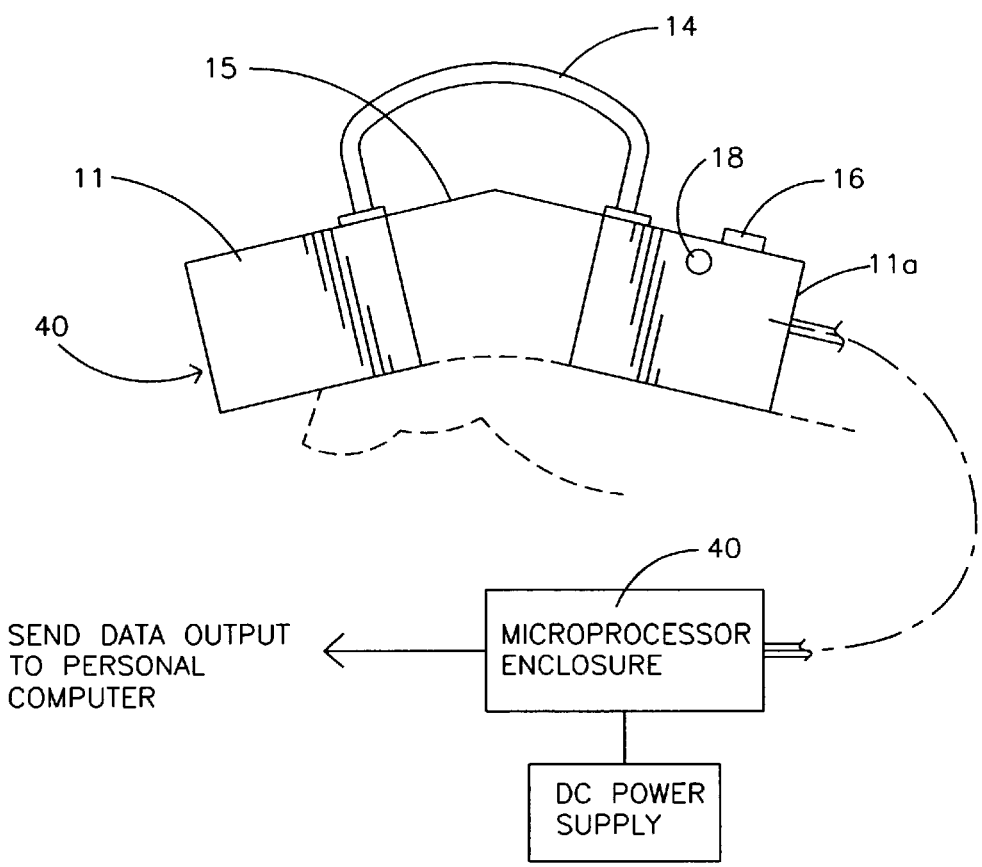
FIG. 1 is a perspective view of the novel miniature inclinometer for angle measurement with accurate measurement indicator.

As shown in the figures, the miniature inclinometer for angle measurement with accurate measurement indicator 10 comprises at least one housing 11 and 11a that contains a pair of inclinometer board assemblies 12 and 13 which are connected by cable 14 and plugs 15. The button 16 shown is used to trigger the microprocessor 40 to gather analog data from the analog to digital converter 17. An indicator light 18 is used to display a number of potential errors in order to prevent a sampling of inaccurate data. The detection of errors due to inertial factors can be accomplished by monitoring the absolute output of either of the sensors 19 and 20, such as accelerometers. The magnitude of the acceleration vector can be calculated from the accelerometer. If this calculated value exceeds one G, an inertial error is communicated to the user. The indicator light 18 is used to communicate this error to the user. The light can also be used to ensure that the inclinometer 10 is not moved during the measurement process. This is accomplished by the microprocessor 40 sampling the sensors 19 and 20, and ensuring that they do not change over the measurement period. The parameters of the error checking are all programmable through a personal computer.

A plurality of control buttons 16 can also be provided that incorporate programmable functions. In addition, sensors 19, 20 can have straps allowing easy attachment to body limbs.

Figure 2:
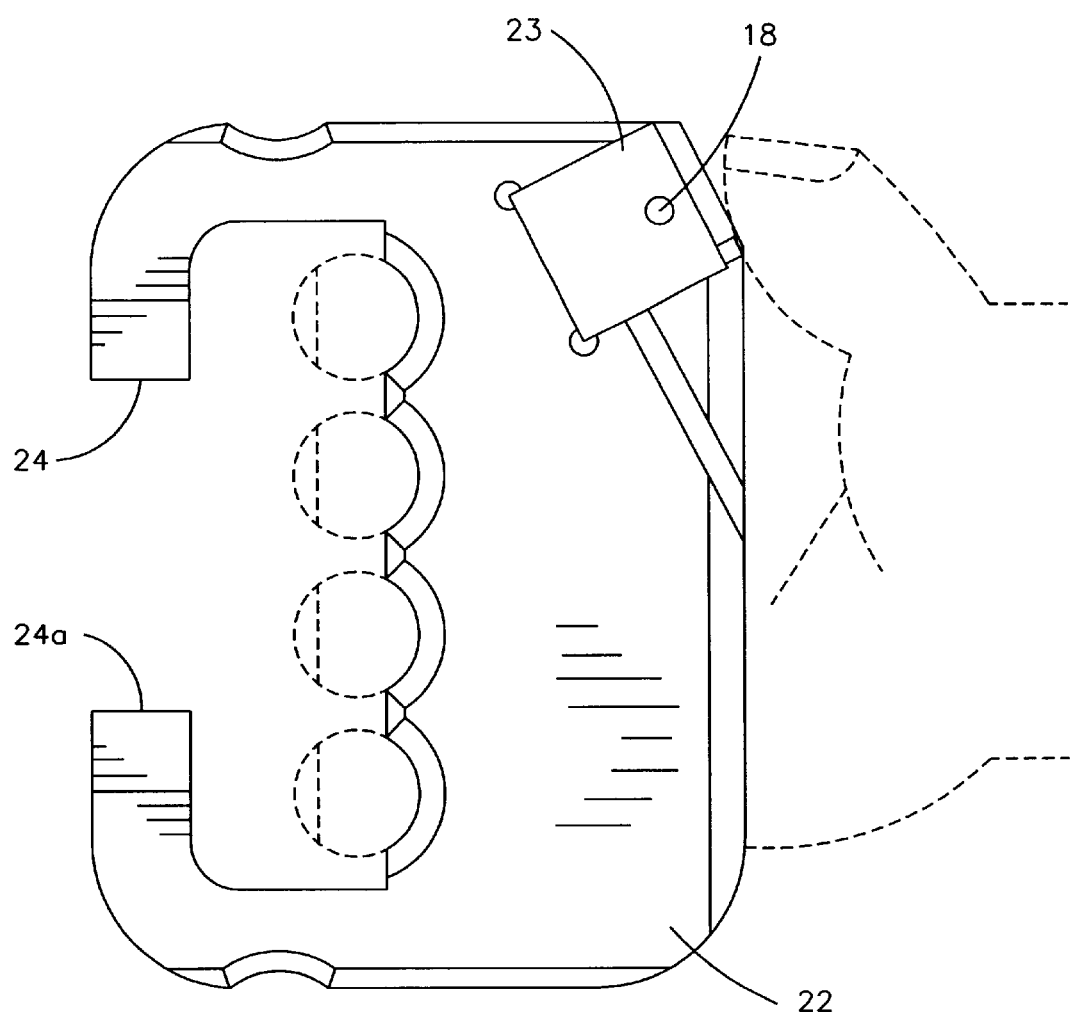
FIG. 2 is a perspective view of an alternate embodiment.
Figure 5:
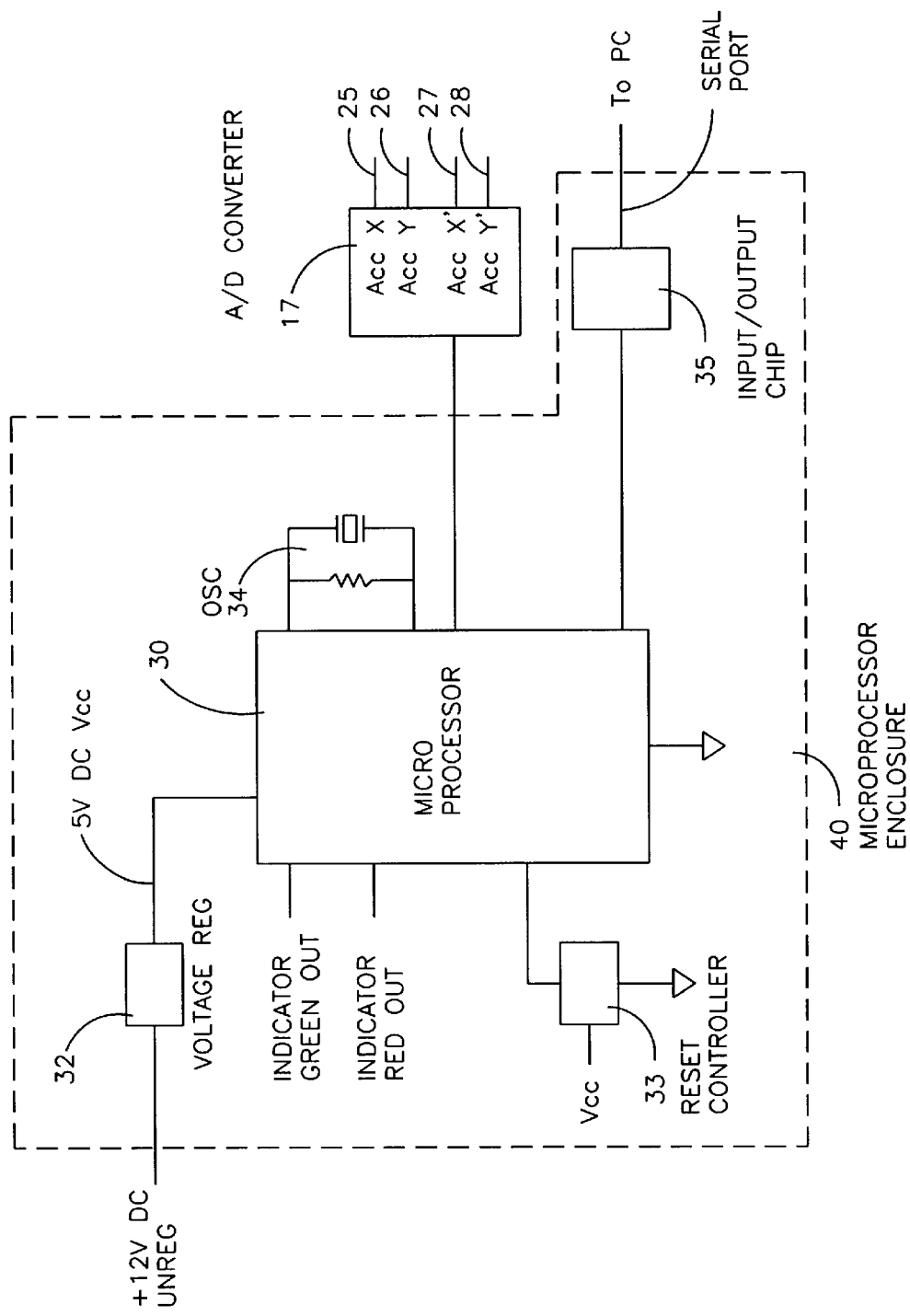
FIG. 5 is a schematic view of the electrical system thereof.

The alternate embodiment shown in FIG. 2 comprises a larger housing 22 that contains an inclinometer 23 and is designed to be used as a hand held device. The prongs 24 and 24a allow the user to accurately place the housing 22 onto a flat or curved surface. The operation of the unit is the same as described for the other embodiment.

The sensors 19 and 20 are pairs of accelerometers, by way of example. They could be pendulum units, fluid filled inclinometers (capacitive, inductive or electrolytic), accelerometer units (peizo resistive, capacitive or open or closed loop servers) or ball bearing type. The accelerometers 19 and 20 are oriented in such a way that their sensitive measuring axis are at an angle of ninety degrees with respect to each other. The analog data is then transmitted from each sensor along conductors 25, 26, 27 and 28. The data is received by an analog to digital converter 17. The digital data is then sent to the multiplexer 30 within the microprocessor 40 by means of a cable 31. Multiplexer 30 allows changing input to microprocessor 40 from one sensor 19, 20 to another sensor 19, 20. The multiplexer 30 receives regulated direct current power from a voltage regulator 32. The microprocessor 40 also contains a reset controller 33 and an oscillator 34. The data from a multiplexer 30 is then sent to an input and output chip 35 which connect to a serial port to communicate with a personal computer where data can be displayed. The data can also be transmitted over a computer network. RS232 input/output chip 35 can be provided for allowing communication to a computer. Microprocessor 40 can also have electrically erasable programmable read only memory for use in storing sensor calibration coefficients and lookup tables for comparing output of sensor 19, 20 to the vertical defined by the force of gravity. Microprocessor 40 can then calculate the angle between the pair of sensors for any angle over a fully 360 degree range of angles.

Figure 6:
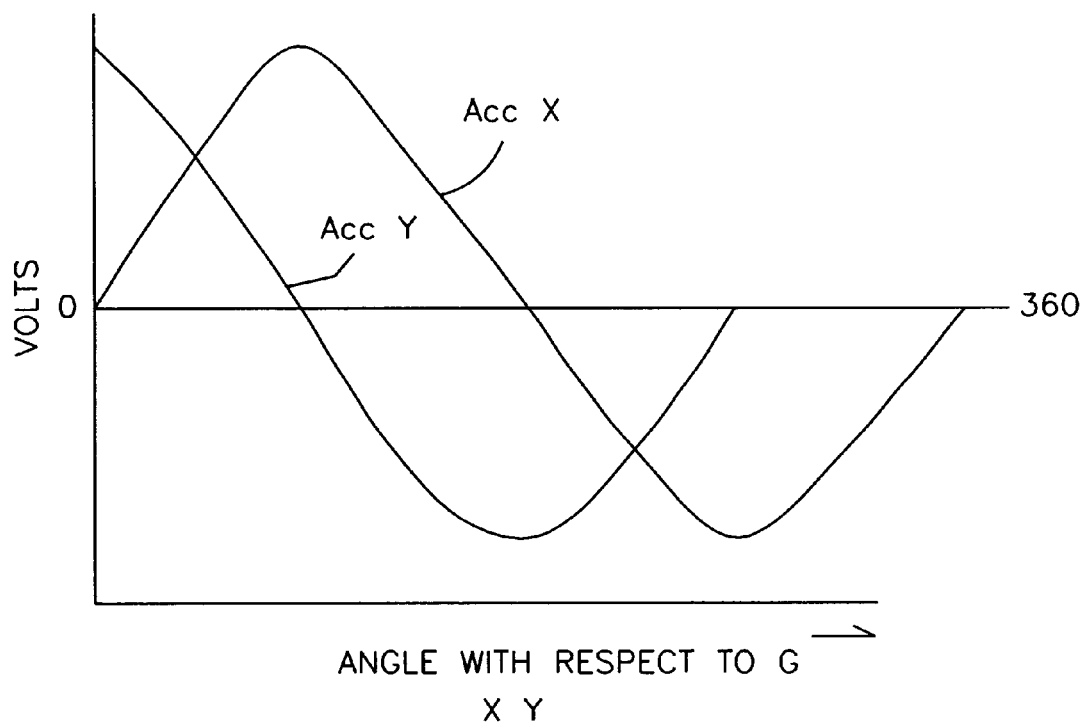
FIG. 6 is a graphical chart showing the voltage output from the sensors.
Figure 6:
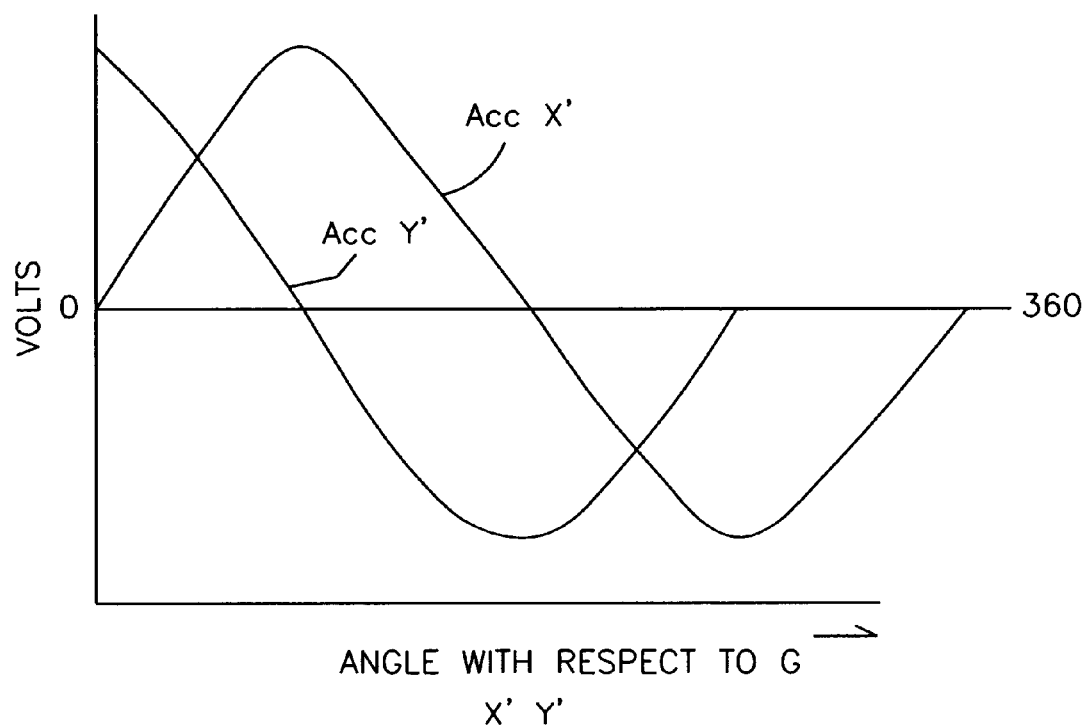

An example of the output from the pairs of accelerometers is graphically charted in FIG. 6 and shown as voltages (Acc X, Acc Y, Acc X' and Acc Y') respectively. The angles are shown with respect to the earth's gravitational field. From these data angles Theta 1 and Theta 2 are found by computing the arc tangent of Acc X/Acc Y and Acc X'/Acc Y' respectively. The data from the sensors positioned within the housing can be used to measure the inclinometers position with respect to the earth's gravity vector. The data from the sensors positioned within the housings may be used to compute the difference angle and indicate the angle of each inclinometer housing with respect to the other.

The operation of the novel miniaturized inclinometer for angle measurement with accurate measurement indicator is designed to provide a number of advantages over current devices. Current devices have been difficult to use to get accurate measurements without restricting the user's movement or having linkages that interfere with the activities taking place. This unit allows the user to positioning the measuring device in such a way to get optimum readings without interfering in those activities. The device is also designed to overcome errors caused by cross axial motions of the limb by means of positioning of the sealed sensors. The self testing activities of the device minimizes the false readings that are possible with other devices.

The present invention also includes a D/A converter that the micro controller programs to provide an analog voltage proportional to the micro processor calculated/lookup angle.

The present invention also includes excitation and decoding circuitry that includes a synchronous demodulator.

While we have described our invention in connection with specific embodiments thereof, it is clearly to be understood that this is done only by way of example and not as a limitation to the scope of our invention as set forth in the objects thereof and in the appended claims.

We claim:

1. A measuring device comprising a sensor, a microprocessor, and an output device, said sensor for providing a measurement to said microprocessor for calculating an angle with respect to the direction of the gravity vector, wherein said microprocessor provides a signal comprising said calculated angle and a self-testing output signal, wherein said self-testing output signal is directed to said output device for indicating whether said sensor measurement is substantially affected by an inertial error, wherein said self-testing output signal indicating inertial error is not combined with said calculated angle signal to provide a corrected calculated angle.

2. The measuring device as recited in claim 1, wherein said output device comprises a light to communicate an error to a user.

3. The measuring device as recited in claim 1, wherein said output device comprises a computer display.

4. The measuring device as recited in claim 1, wherein said microprocessor is adapted to sample said sensor over a period of time, and said microprocessor is adapted so that said self-testing output signal indicates that no error exists if said measurement does not substantially change over said measurement period.

5. The measuring device as recited in claim 1, wherein said microprocessor is adapted to calculate magnitude of acceleration vector, and said microprocessor is adapted so that said self-testing output signal communicates an error signal if said magnitude exceeds the acceleration due to gravity.

6. The measuring device as recited in claim 1, wherein said sensor comprises an accelerometer, a pendulum unit, a fluid filled inclinometer, or a ball bearing inclinometer.

7. The measuring device as recited in claim 1, wherein said measuring device further comprises a plurality of said sensors and a multiplexer for directing data from said plurality of sensors.

8. The measuring device as recited in claim 1, further comprising an activator to trigger said microprocessor to gather data.

9. The measuring device as recited in claim 8, wherein said activator comprises a button controllable by an operator.

10. The measuring device as recited in claim 1, wherein said measuring device further comprises a plurality of said sensors.

11. The measuring device as recited in claim 10, wherein each said sensor comprises an accelerometer.

12. The measuring device as recited in claim 10, wherein said plurality of sensors comprise a pair of sensors arranged with their measuring axis at an angle with respect to each other.

13. The measuring device as recited in claim 12, wherein said pair of sensors are arranged with said measuring axis orthogonal to each other.

14. The measuring device as recited in claim 12, wherein said plurality of sensors comprises two of said pairs of sensors to measure a difference between two directions in a single measurement to provide an angle there between.

15. The measuring device as recited in claim 1, wherein said measuring device is adapted to measure angles on joints of a person.

16. The measuring device as recited in claim 15, wherein said measuring device comprises straps for attaching to said person.

17. The measuring device as recited in claim 1, wherein said measuring device is adapted to measure an angle between two body surfaces without linkages being provided there between.

18. The measuring device as recited in claim 1, wherein said measuring device is hand held and is for holding to a surface.

19. The measuring device as recited in claim 1, wherein said microprocessor comprises an erasable programmable read only memory.

20. The measuring device as recited in claim 19, wherein said erasable programmable read only memory is for storing sensor calibration coefficients and lookup tables for comparing an angle defined by sensor output to the direction of the gravity vector.

21. The measuring device as recited in claim 1, wherein said microprocessor is connected to a computer.

22. The measuring device as recited in claim 21, wherein parameters of said self-testing are programmable through said personal computer.

23. The measuring device as recited in claim 21, wherein said microprocessor is connected to a network of computers.

24. The measuring device as recited in claim 21, wherein said measuring device further comprises an input/output comprising a serial port for providing output data to said computer.

25. The measuring device as recited in claim 1, wherein said measuring device further comprises a voltage regulator for providing a regulated voltage to said microprocessor.

26. The measuring device as recited in claim 1, wherein said measuring device is adapted to calculate angles over a full 360 degrees.

27. The measuring device as recited in claim 1, wherein sampling data is prevented if said inertial error is present.

28. A method of measuring an angle comprising the steps of
a) providing an inclinometer sensor having a self-testing feature; and
b) initiating an angle measurement with said inclinometer sensor, wherein said self-testing feature provides an output signal indicating whether said measurement is substantially affected by an inertial error during said measurement, wherein said self-testing output signal indicating inertial error is not combined with said measurement to provide a corrected measurement angle.

29. The method as recited in claim 28, further comprising the step of displaying whether said measurement is substantially effected by said inertial errors during said measurement.

30. The method as recited in claim 29, wherein said displaying step comprises turning on or off a light to communicate an error to a user.

31. The method as recited in claim 29, wherein said displaying step comprises providing said self-testing output signal on a line to a computer display.

32. The method as recited in claim 28, wherein said self-testing comprises sampling said sensor over a period of time, wherein if said measurement does not substantially change over said measurement period said self-testing output signal does not indicate an error.

33. The method as recited in claim 28, wherein said self-testing comprises calculating magnitude of acceleration vector, and displaying an error if said magnitude exceeds the acceleration due to gravity.

34. The method as recited in claim 28, wherein said sensor comprises an accelerometer, a pendulum unit, a fluid filled inclinometer, or a ball bearing inclinometer.

35. The method as recited in claim 28, wherein said providing step (a) further comprises providing a plurality of said inclinometer sensors.

36. The method as recited in claim 35, wherein each said sensor comprises an accelerometer.

37. The method as recited in claim 35, wherein said plurality of sensors comprise a pair of sensors arranged with their measuring axis at an angle with respect to each other.

38. The method as recited in claim 37, wherein said pair of sensors are arranged with said measuring axis orthogonal to each other.

39. The method as recited in claim 37, wherein said plurality of sensors comprise two of said pairs of sensors to measure a difference between two directions in a single measurement to provide an angle there between.

40. The method as recited in claim 28, wherein said sensor is for measuring an angle in a plurality of sequential measurements.

41. The method as recited in claim 28, wherein in said initiating a measurement step (b) said sensor is adapted to measure angles on joints of a person.

42. The method as recited in claim 41, wherein said sensor is adapted to measure said angle without providing linkages there between.

43. The method as recited in claim 28, wherein said initiating a measurement step (b) comprises holding said sensor to a surface.

44. The method as recited in claim 28, wherein said sensor is adapted to calculate angles over a full 360 degrees.

45. An angle measuring device comprising a housing, a sensor and a processor, wherein said sensor and said processor are both in said housing, wherein said sensor for sensing and said processor are for sensing and calculating an angle with a continuous range of 360 degrees with respect to the direction of the gravity vector, said sensor comprising a first accelerometer and a second accelerometer, wherein said first accelerometer has a first sensitive measuring axis oriented in a first direction and said second accelerometer has a second sensitive measuring axis oriented in a second direction, wherein said first direction is different from said second direction.

46. The measuring device as recited in claim 45, wherein said first sensitive measuring axis is orthogonal to said second sensitive measuring axis.

47. The measuring device as recited in claim 45, further comprising an analog to digital converter, wherein said accelerometers are connected to said processor through said analog to digital converter.

48. The measuring device as recited in claim 45, wherein said measuring device further comprises a plurality of said sensors.

49. The measuring device as recited in claim 44, wherein said measuring device further comprises a multiplexer for directing data from said plurality of sensors.

50. The measuring device as recited in claim 48, wherein said plurality of sensors comprise two of said sensors, wherein said device measures a difference between two directions in a single measurement to provide an angle there between.

51. The measuring device as recited in claim 45, wherein said measuring device further comprises an activator to trigger said processor to gather data.

52. The measuring device as recited in claim 45, wherein said processor comprises an erasable programmable read only memory.

53. The measuring device as recited in claim 52, wherein said erasable programmable read only memory is for storing sensor calibration coefficients and lookup tables for comparing an angle defined by sensor output to the direction of the gravity vector.

54. The measuring device as recited in claim 45, wherein said processor is connected to a computer.

55. The measuring device as recited in claim 54, wherein said measuring device further comprises an input/output comprising a serial port for providing output data to said computer.

56. The measuring device as recited in claim 45, wherein said processor is connected to a network of computers.

57. The measuring device as recited in claim 45, wherein said measuring device further comprises a voltage regulator for providing a regulated voltage to said processor.

58. The measuring device as recited in claim 45, wherein said processor provides a signal comprising said calculated angle and a self-testing output signal, wherein said self testing output signal is directed to said output device for indicating whether said sensor measurement is substantially effected by an inertial error, wherein said self-testing output signal indicating inertial error is a separate signal from said calculated angle signal.

59. The measuring device as recited in claim 45, wherein said output device comprises a light to communicate an error to a user.

60. The measuring device as recited in claim 45, wherein said output device comprises a computer display.

61. The measuring device as recited in claim 45, wherein said microprocessor is adapted to sample said sensor over a period of time, and said microprocessor provides no output signal indicating an error if said measurement does not substantially change over said measurement period.

62. The measuring device as recited in claim 45, wherein said microprocessor is adapted to sample said sensor over a period of time, and said microprocessor provides an output signal indicating that no error exists if said measurement does not substantially change over said measurement period.

63. The measuring device as recited in claim 45, wherein said device is adapted to calculate magnitude of acceleration vector, and if said magnitude exceeds the acceleration due to gravity an inertial error is communicated.

64. The measuring device as recited in claim 45, wherein said housing further comprises strapping for allowing ease of attachment to body limbs.

65. The measuring device as recited in claim 45, wherein said processor further comprises programmable functions.

66. The measuring device as recited in claim 45, wherein said processor further comprises lookup tables.

67. The measuring device as recited in claim 45, further comprising a synchronous demodulator.

68. The measuring device as recited in claim 45, wherein said processor further comprises an RS232 input/output chip for external communication.

69. The measuring device as recited in claim 45, wherein said housing comprises a first portion and a second portion and wherein said sensor is in said first portion and said processor is in said second portion.

* * * * *